Figure 1:
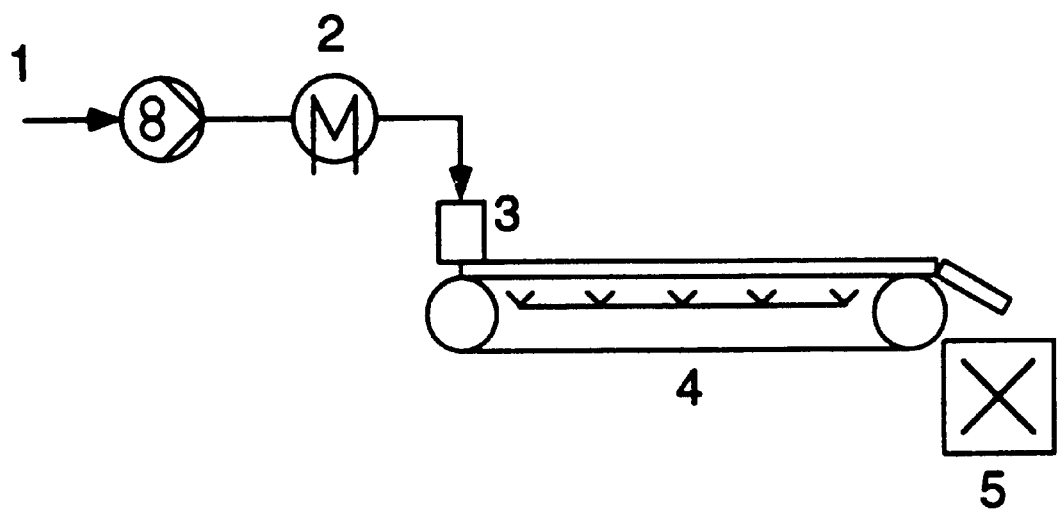

United States Patent [19]

Melder et al.

[11] Patent Number: 5,936,115
[45] Date of Patent: Aug. 10, 1999

[54] PRODUCTION OF CLUMPING-FREE NEOPENTYL GLYCOL HYDROXPIVALATE GRANULES

[75] Inventors: Johann-Peter Melder, Neuhofen; Dieter Baumann, Frankenthal; Bernhard Maltry, Obrigheim, all of Germany

[73] Assignee: BASF Aktiengesellschaft, Ludwigshafen, Germany

[21] Appl. No.: 09/092,983

[22] Filed: Jun. 8, 1998

[30] Foreign Application Priority Data

Jun. 10, 1997 [DE] Germany .......................... 197 24 461

[51] Int. Cl.⁶ .................................................. C07C 69/66
[52] U.S. Cl. ............................................................ 560/189
[58] Field of Search ............................................... 560/189

[56] References Cited

U.S. PATENT DOCUMENTS 4,769,200  9/1988  Hupfer et al. .......................... 264/143
5,445,108  8/1995  Schermutzki et al. .................. 117/200

FOREIGN PATENT DOCUMENTS 829298    9/1997  European Pat. Off. .
1222891   4/1959  Germany .
3522359   6/1985  Germany .

*Primary Examiner*—Paul J. Killos
*Attorney, Agent, or Firm*—Keil & Weinkauf

[57] ABSTRACT

In a process for the production of neopentyl glycol hydroxypivalate granules by depositing a neopentyl glycol hydroxypivalate melt on a chill surface, on which the melt solidifies, as a flat film, which, after solidification, is comminuted to give granules. The melt contains less than 3% by weight, based on the total amount of neopentyl glycol hydroxypivalate, of neopentyl glycol hydroxypivalate crystals.

8 Claims, 1 Drawing Sheet

PRODUCTION OF CLUMPING-FREE NEOPENTYL GLYCOL HYDROXPIVALATE GRANULES

The invention relates to a process for the production of clumping-free neopentyl glycol hydroxypivalate granules, to the granules obtained, and to the use of a granulation device for the production of the granules.

Neopentyl glycol hydroxypivalate (NGHP) is used, inter alia, as a constituent of food can internal coatings in order to increase the impact strength thereof. For conversion into granules, an NGHP melt is deposited on a chill belt via a drop former. This gives flat, flake-shaped granules which tend to clump on storage in drums.

Clumping hinders metering and removal of the granules from the drums.

DE-A-35 22 359 discloses a process for the granulation of crystalline, organic materials, such as neopentyl glycol hydroxypivalate, which gives a product having improved flow properties. In this process, a twin-screw compounder having co-rotating screws is used to compact a pulverulent material or to crystallize and compact a molten material, at material temperatures from about 1 to 20° C. below the melting point of the material employed. The material is then ejected through a heated pelletizing die into a low-pressure zone. The pelletizing die is warmed to a temperature of from 1 to 30° C. above the melting point of the material, so that the individual crystals conveyed past the wall of the die melt to form a film, which, after solidification, forms a solid corset for the compacted crystalline material. The material extrudates are then comminuted in a subsequent zone and cooled. The flow properties of the resultant granules are not adequate for all applications.

It is an object of the present invention to provide a process for the production of clumping-free NGHP granules which avoids the disadvantages of known processes.

We have found that this object is achieved by a process for the production of neopentyl glycol hydroxypivalate granules in which a neopentyl glycol hydroxypivalate melt is deposited on a chill surface, on which the melt solidifies, which comprises depositing the neopentyl glycol hydroxypivalate melt, which contains less than 3% by weight, based on the total amount of neopentyl glycol hydroxypivalate, of neopentyl glycol hydroxypivalate crystals, on the chill surface as a flat film, which, after solidification, is comminuted to give granules.

The novel process allows the production of NGHP granules which have no tendency to clump in drums, since the individual granules have high hardness and low plasticity.

In granules produced from crystal-seeded melts or thin films, the structure is built up from crystallites which are present in the melt and continue to grow therein. The solid ultimately has a large number of grain interfaces, which are movable with respect to one another and impart plasticity on the solid. The application of pressure causes the contact points between the particles to flatten and consequently increase in size, which causes the generation of large adhesive forces through cohesion. On solidification of an NGHP film, from a melt having a low or preferably zero crystal content, a solid is formed which has a highly ordered structure. This means that granules which have broken off this solidified film have high hardness and low plasticity, which prevents flattening of particulate contact points in drums. The generation of adhesive forces through cohesion can thus be avoided.

Before cooling, the melt preferably contains less than 1% by weight, particularly preferably less than 0.5% by weight, based on the total amount of NGHP, of NGHP crystals. In particular, the melt is essentially or completely free from NGHP crystals. Before deposition on the chill surface, the melt is preferably cooled in a precooler to a temperature close to the melting point. For NGHP, this temperature is in the region of 50° C. The passage through the precooler can be adjusted so that no crystals are present in the melt at the precrystallizer outlet.

The melt is preferably deposited on the chill surface, preferably a chill belt, in such a way that the thickness of the flat film is at least 2 mm, particularly preferably from 5 to 20 mm. After complete solidification, the flat film is then comminuted in a breaker.

The invention is illustrated in greater detail below with reference to the drawing, in which FIG. 1 shows an apparatus for the production of NGHP granules in which

| | |
|---|---|
| 1 | denotes the NGHP melt |
| 2 | denotes the precooler |
| 3 | denotes a deposition system |
| 4 | denotes the chill melt and |
| 5 | denotes the breaker. |

The apparatus used in accordance with the invention is known per se. An apparatus of this type is described, for example, in DE-A-28 47 887, which gives further details on suitable deposition systems.

In the embodiment shown in FIG. 1, the NGHP melt (1) is firstly passed through a precooler (2). The hot, liquid NGHP melt is cooled in the precooler (2) to a temperature in the region of the melting point (50° C.). The precooled melt is then deposited, via a deposition system (3), on a continuously driven chill belt (4), and solidifies thereon.

The deposition system (3) is designed so that the melt is distributed over essentially the entire width of the chill belt (4). To this end, the chill belt may be provided with an edge lip in order to achieve a uniform film thickness over the entire width of the belt. The thickness of the flat film formed in this way is preferably at least 2 mm, particularly preferably from 5 to 20 mm, in particular from 5 to 15 mm.

At the end of the continuous belt, the solidified film breaks off, for example owing to gravity, and is comminuted fiber in a breaker (5), giving flat granules having a mean particle diameter of from 3 to 50 mm, preferably from 4 to 30 mm, in particular from 5 to 20 mm. These NGHP granules preferably have a cuboid or isometric shape. The NGHP granules obtained have a very low tendency to clump.

The invention furthermore relates to the use of a granulation device for a melt, comprising, connected in series via feed lines, a precooler (2), a deposition system (3) for depositing the melt on a subsequent chill belt (4), which is followed by a breaker (5) for granulation of neopentyl glycol hydroxypivalate. The melt has the composition given above.

The novel granules have higher bulk density and better meterability than known granules. In particular, the essentially spherical granules are easy to meter and have very high bulk density.

We claim:

1. A process for the production of neopentyl glycol hydroxypivalate granules in which a neopentyl glycol hydroxypivalate melt is deposited on a chill surface, on which the melt solidifies, which comprises depositing the neopentyl glycol hydroxypivalate melt, which contains less than 3% by weight, based on the total amount of neopentyl glycol hydroxypivalate, of neopentyl glycol hydroxypivalate crystals, on the chill surface as a flat film, which, after solidification, is comminuted to give granules.

2. A process as claimed in claim 1, wherein the melt contains less than 1% by weight, based on the total amount of neopentyl glycol hydroxypivalate, of neopentyl glycol hydroxypivalate crystals.

3. A process as claimed in claim 1, wherein the melt is essentially free from neopentyl glycol hydroxypivalate crystals.

4. A process as claimed in claim 1, wherein the thickness of the flat film is at least 2 mm.

5. A process as claimed in claim 4, wherein the thickness of the flat film is from 5 to 20 mm.

6. A process as claimed in claim 1, wherein the neopentyl glycol hydroxypivalate melt is firstly passed through a precooler and is then deposited, via a deposition system, on a continuously driven chill belt, solidifies thereon, and, after leaving the chill belt, is converted into granules in a breaker.

7. Neopentyl glycol hydroxypivalate granules obtainable by a process as defined in claim 1.

8. A process as claimed in claim 1, involving the use of a granulation device for a melt, comprising, connected in series via feed lines, a precooler (2), a deposition system (3) for depositing the melt on a subsequent chill belt (4), which is followed by a breaker (5) for the granulation of the neopentyl glycol hydroxypivalate.

\* \* \* \* \*